United States Patent [19]

Tsumura et al.

[11] 4,080,391

[45] Mar. 21, 1978

[54] PROCESS FOR THE PRODUCTION OF ALCOHOLS

[75] Inventors: Ryuichiro Tsumura; Toru Takahashi, both of Fujisawa; Toshiyuki Ichikawa, Tokyo; Muneaki Kanemaru; Norimichi Ishii, both of Kawasaki, all of Japan

[73] Assignee: Mitsui Toatsu Chemicals, Tokyo, Japan

[21] Appl. No.: 651,729

[22] Filed: Jan. 23, 1976

Related U.S. Application Data

[63] Continuation-in-part of Ser. No. 281,371, Aug. 17, 1972, abandoned.

[30] Foreign Application Priority Data

Aug. 26, 1971  Japan .................................. 46/64745

[51] Int. Cl.$^2$ ............................................... C07C 29/04
[52] U.S. Cl. ..................................... 260/641; 260/503; 260/505 R; 260/513 R; 260/614 R
[58] Field of Search ......................................... 260/641

[56] References Cited

U.S. PATENT DOCUMENTS

| 2,720,547 | 10/1955 | Wolff et al. .................... 260/614 A |
|---|---|---|
| 2,830,091 | 4/1958 | Friedman et al. ............... 260/614 A |
| 3,006,970 | 10/1961 | Beuther et al. ....................... 260/641 |
| 3,256,250 | 6/1966 | Frilette ................................ 260/641 |
| 3,455,664 | 7/1969 | Rosscup et al. ..................... 260/641 |
| 3,555,080 | 1/1971 | Resnick ............................ 260/513 R |

*Primary Examiner*—Joseph E. Evans
*Attorney, Agent, or Firm*—Fisher, Christen & Sabol

[57] ABSTRACT

A process for the production of alcohols by the direct hydration of an olefin with water under liquid phase hydration conditions and in the presence of a catalytic amount of a sulfonic acid catalyst represented by the general formulae (1) or (2)

$$ACF_2SO_3H \quad (1)$$

$$B(CF_2SO_3H)_n \quad (2)$$

wherein A represents hydrogen, halogen, a sulfonic radical, a sulfodifluoromethyl radical or a monovalent unsubstituted aliphatic, alicyclic or aromatic residue consisting of hydrocarbon or fluorohydrocarbon radicals containing less than 20 carbon atoms and B represents a di-, tri- or tetravalent unsubstituted aliphatic, alicyclic or aromatic residue consisting of hydrocarbon or fluorohydrocarbon radicals containing less than 20 carbon atoms in direct corresponding to the value of n being 2, 3 or 4.

7 Claims, No Drawings

4,080,391

PROCESS FOR THE PRODUCTION OF ALCOHOLS

CROSS-REFERENCE TO RELATED APPLICATION

This application is a continuation-in-part of copending application Ser. No. 281,371 filed Aug. 17, 1972 now abandoned.

BACKGROUND OF THE INVENTION

1. Field of the Invention

The present invention relates to a method for the production of alcohols and, more particularly, to the direct hydration of olefins with water under liquid phase hydration conditions and in the presence of a catalyst to produce said alcohols.

2. Description of the Prior Art

Various direct hydration methods for producing alcohols by hydrating olefins in the presence of an acidic catalyst are well known in the art including vapor phase and liquid phase hydrations under low pressure conditions, or mixed phase and liquid phase hydrations under high pressure conditions, using a fixed bed catalyst, a suspension catalyst, soluble catalyst and the like.

However, in the production of ethanol from ethylene, or isopropanol from propylene, the direct hydration method currently employed on an industrial scale is a low pressure vapor phase method using a fixed bed catalyst of phosphoric acid. This method requires temperatures approaching 300° C. to accelerate the reaction velocity. Moreover, since the reaction is carried out in the vapor phase, it is necessary to maintain a mole ratio of water to the olefin used as starting material at 1 or less and to conduct the hydration reaction under a relatively low pressure, for example, of 40–80 kg/cm². As a result, conversion of the olefin is usually only several precent, and cannot be greater than that value due to its chemical equilibrium.

Extensive studies have been conducted on catalystic hydration in a mixed phase or in a liquid phase containing a solid acid such as alumina, silica-alumina, tungsten oxide, molybdenum oxide or chromium oxide, a heteropoly acid containing therein tungsten or molybdenum, an inorganic acid such as phosphoric acid or sulfuric acid, or an organic acid such as sulfonic acid, a carboxylic acid or an acidic ion exchange resin. As typical of such sulfonic acid catalysts, U.S. Pat. No. 3,455,664, for instance, discloses the hydration of water and isopropylene using a catalyst such as sulfonic acid in the liquid phase at a temperature of from 200° to 550° F. under a pressure of from 2,000 to 100,000 p.s.i. U.S. Pat. No. 3,555,080, on the other hand, teaches that sulfonyl-containing fluorocarbon ethers expressed by the formula

wherein X is fluorine and M is a hydroxyl group, and derivatives thereof in the sulfonic acid form are useful as an acid catalyst for the acid-catalyzed reaction, but specific and definite examples of such reactions are not illustrated. Further, U.S. Pat. No. 2,830,091 teaches a method wherein an olefin is hydrated in the liquid phase at a temperature of 250°–400° F. and a pressure of 500–3,000 p.s.i. with the aid of a certain fluoridated polycarboxylic acid. However, these known catalysts have disadvantages in one or more of their activity, selectivity, catalytic stability or noncorrosion characteristics and have not yet been put into practical use.

SUMMARY OF THE INVENTION

It is a primary object of the present invention to provide an improved process for the direct liquid phase hydration of an olefin with water using a novel sulfonic acid catalyst.

A further object of the present invention is to provide such a sulfonic acid catalyst which exhibits satisfactory hydration activity in small catalytic amounts.

Another object of the present invention is to provide such a catalyst which allows extremely high selectively without producing any low-molecular-weight polymer due to undesirable polymerization of the olefin used.

Still another object of the present invention is to provide such a catalyst which has a long active life and which is free from thermal decomposition which easily occurs with known catalysts such as a conventional sulfonic acid or a cation exchange resin containing the sulfonic acid radical as an exchange radical.

Yet another object of the present invention is to provide such a catalyst having little or no corrosive effect on materials of an apparatus even in the strongly acidic range of the hydration reaction.

A still further object of the present invention is to provide a novel catalyst which can produce, if desired, ethers during the preparation of alcohols at elevated temperatures by contacting olefins with water in a liquid phase.

Still further objects and the entire scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

It has been found that the above objects are attained by a direct liquid phase hydration of an olefin to give the corresponding alcohol or an ether at the same time, if desired, in the presence of a catalyst expressed by general formulae (1) and/or (2)

wherein A represents hydrogen, halogen, a sulfonic radical, a sulfodifluoromethyl radical or a monovalent unsubstituted aliphatic, alicyclic or aromatic residue consisting of hydrocarbon or fluorohydrocarbon radicals containing less than 20 carbon atoms, and B represents a di-, tri- or tetra-valent unsubstituted aliphatic, alicyclic and aromatic residue consisting of hydrocarbon or fluorohydrocarbon radicals containing less than 20 carbon atoms in direct correspondence to the value of n being 2, 3 or 4.

Furthermore, in accordance with the method of the present invention, the interaction of an olefin and water in the presence of the above-mentioned catalyst produces the corresponding alcohol alone or the alcohol and an ether at the same time if desired, with high conversion and high selectivity, and without loss of the catalyst used or difficulty in the selection of materials for the apparatus.

DESCRIPTION OF THE PREFERRED EMBODIMENTS

In the broader aspect, compounds useful as a catalyst in the method of the present invention may be defined as sulfonic acids having one or more sulfonic acid radicals attached to a trifluoromethyl radical or to difluoromethylene radicals. Sulfonic acids in which hydrogen atoms are partially substituted by fluorine atoms may be used as the catalyst, although sulfonic acids in which all hydrogen atoms attached to carbon atoms are substituted by fluorine atoms are preferred.

These sulfonic acids can be prepared by conventional methods, for instance: by hydrolysis following fluorine-substitution by electrolyzing sulfonic acids in an atmosphere containing hydrogen fluoride; by hydrolyzing fluoroalkylsulfonyl chloride obtained by oxidizing fluoroalkyldisulfide; by adding sodium sulfite to a fluoroolefin; or by oxidizing a fluoro-substituted thiol. These methods are disclosed in, for example, Fluorine Chemistry Review, Vol. 4, 1969, edited by P. Tarrant and Organic fluorine Chemistry, 1969, written by W. A. Sheppard and C. M. Sharts.

The following compounds can particularly be used as the catalyst of the present invention. In the above-disclosed general formula (1): difluoromethane sulfonic acid where A is hydrogen; trifluoromethane sulfonic acid and chlorodifluoromethane sulfonic acid where A is hydrogen; difluoromethionic acid where A is a sulfonic acid radical; perfluoro-1,2-disulfonic acid where A is a sulfodifluoromethyl radical; perfluoroethanesulfonic acid, 1,1,2,2-tetrafluoroethane sulfonic acid, 1,1-difluoroethane sulfonic acid, perfluoropropane sulfonic acid, β-H-perfluoropropane sulfonic acid, perfluorobutane sulfonic acid, perfluoropentane sulfonic acid, β-H-perfluoropentane sulfonic acid, perfluorohexane sulfonic acid, perfluoroheptane sulfonic acid, perfluorooctane sulfonic acid, β-H-perfluorooctane sulfonic acid, perfluorodecane sulfonic acid and perfluorododecane sulfonic acid where A is a monovalent unsubstituted aliphatic residue; cyclohexyl difluromethane sulfonic acid and 2-perfluorocyclohexyl tetrafluoroethane sulfonic acid where A is a monovalent unsubstituted alicyclic residue; and phenyl difluoromethane sulfonic acid, p-fluorophenyl difluoromethane sulfonic acid, perfluorotoluene-ω-sulfonic acid and perfluorotoluene-4,ω-disulfonic acid where A is a monovalent unsubstituted aromatic residue;

In the general formula (2): perfluoropropane-1,3-disulfonic acid, perfluorobutane-1,4-disulfonic acid, 1,4-bis(sulfodifluoromethyl)cyclohexane, 1,4-bis(sulfodifluoromethyl)perfluorocyclohexane, 1,4-bis(sulfodifluoromethyl)benzene and 1,4-bis(sulfodifluoromethyl)perfluorobenzene where n is 2; fluorotris(sulfodifluoromethyl)methane, 1,2,3-tris(sulfodifluoromethyl)perfluoropropane, and 1,3,5-tris(sulfodifluoromethyl)benzene where n is 3; and tetrakis(sulfodifluoromethyl)methane and tetrakis(sulfodifluoromethyl)biphenyl where n is 4.

The olefins which are used to give the corresponding alcohols and/or ethers in accordance with the method of the present invention may contain from 2 to 20 carbon atoms. The typical olefins include, for example, ethylene, propylene, n-butene, isobutene, pentene, hexene, octene, dodecene, octadecene, etc.

The direct hydration reaction of the olefins in accordance with the method of the present invention is carried out by contacting an olefin at elevated temperature and in a predetermined mole ratio with water containing a sulfonic acid catalyst which contains a $CF_2SO_3H$ group and may be used in a homogeneous system. Since the catalyst is usually dissolved in the water at the reaction conditions, the reaction efficiently proceeds in the form of an aqueous homogeneous system. Particularly, where an ether is prepared together with the alcohol, the reaction system is separated into two layers since the produced ether forms an organic layer, with the catalyst distributed in both layers.

The amount of catalyst used is in the range of from 0.01 to 2.0% by weight of water introduced in the reaction system, preferably from 0.1 to 1.0% by weight. When the amount of the catalyst used is less than 0.01% by weight, the reaction temperature must be elevated to a temperature higher than the maximum limit specified in the present invention in order to promote the reaction speed thereby resulting in undesirable side-effects. On the other hand, when the amount of the catalyst exceeds 2.0% by weight, the hydration reaction per se of the olefin is not deliteriously affected, but it is not economical.

As to the composition to be reacted, it is advantageous from the standpoint of chemical equilibrium that the mole ratio of water to olefin be maintained as great as possible, and the ratio is generally in the range of from 1:1 to 20:1. However, the mole ratio may be varied depending on the kind of olefin used, i.e., with ethylene or propylene, the mole ratio may suitably be in the range of from 5:1 to 20:1 and with butene, from 3:1 to 15:1. If the molar ratio of water to the olefin is less than 1:1, the hydration reaction of the olefin is extremely deteriorated, and if the molar ratio exceeds 20, separation and recovery of the intended olefin from the hydration reaction products is complicated and results in economical disadvantages.

The reaction advantageously proceeds when conducted at a temperature as low as possible from the standpoint of chemical equilibrium. To an advantage, the catalyst of the present invention has a feature that it is excellent because of exhibiting extremely high acidity. The hydration reaction can be conducted at a temperature higher than that of hydrations by highly concentrated sulfonic acids but lower than that of known vapor phase methods. Generally, the reaction is conducted at a temperature in the range of from 100° to 350° C. With ethylene or propylene, the reaction temperature is preferably in the range of from 250° to 300° C. and 150° to 250° C., respectively, and with butene, in the range of from 100° to 250° C. When the reaction temperature is lower than 100° C., the hydration reaction speed is lowered to an unsatisfactory degree. On the other hand, if the reaction is conducted at a temperature higher than 350° C., thermal decomposition of the catalysts disadvantageously increases to more than negligible amounts.

The reaction pressure should be determined in such a manner that the reaction system is maintained in the liquid phase during the reaction. Although the reaction pressure is varied according to the kind of olefin used, the mole ratio of starting materials, the reaction temperature, etc., it is preferred to use a pressure higher than that required to maintain the water used as starting material in the liquid state under the reaction conditions. Moreover, from the standpoint of chemical equilibrium and reaction kinetics, it is desirable to maintain the pressure as high as possible. Generally, the reaction is conducted under a pressure in the range of from 1 to 500 kg/cm$^2$(G) and a pressurized inert gas can be used in the reaction, if necessary. With ethylene or propylene, the pressure is preferably in the range of from 150 to 350 kg/cm$^2$(G). When the reaction pressure is less than 1 kg/cm$^2$(G), it is difficult or impossible to maintain the reaction system in the liquid phase. On the other hand, pressures exceeding 500 kg/cm$^2$(G) result in the selection of otherwise unnecessary and undesirable reaction conditions.

The alcohol and/or ether of the present invention can easily be produced from the corresponding olefin under the abovedescribed reaction conditions using known batchwise or continuous direct hydration reaction apparatus. In order to effectively carry out the reaction, a continuous system using a reactor vessel having an agitator or a tubular type reactor is preferred. In a liquid phase continuous method, an aqueous solution containing the catalyst and the olefin are reacted with each other by effective contact in parallel current flow or in countercurrent flow through a conventional absorption tower. Then, unreacted oelfin and the reaction product of the ether or alcohol can be separated by distillation or fractional extraction from the reaction solution discharged from the reaction tower. The aqueous solution containing the catalyst is recovered and returned to the reaction tower, so that the catalyst can repeatedly be used without decomposition.

Where an ether together with an alcohol is prepared from an olefin in accordance with the method of the present invention, the following should be taken into consideration. The ether producing reaction occurs only when the hydration reaction of the olefin proceeds to provide a high alcohol concentration in the reaction system. In other words, the ether is mainly formed by a bimolecular dehydration reaction of the alcohol produced in the reaction system. Accordingly, where the purpose of production is directed to the alcohol, per se, the reaction should be terminated at least at the stage of commencement of formation of the ether by a suitable method, i.e., by cooling. On the other hand, for producing the ether at the same time, the ether can be prepared from an olefin in one and the same direct process by prolonging the reaction time, or separated from the alcohol. The ether can more advantageously be produced by increasing the concentration of the catalyst used or by raising the reaction temperature.

Heretofore, strongly acidic cation exchange resins containing aromatic sulfonic acid radicals, or ordinary aromatic sulfonic acids themselves have been an object of research for acid catalysts, but these acid catalysts are lacking in thermal stability, i.e., decomposition of the catalysts easily occurs at a temperature higher than 150° C. in the presence of pressurized water as reported by C. M. Sifter in "The Organic Chemistry of Sulfur" (1948), page 388. Accordingly, these catalysts cannot be used as hydration catalyst for ethylene or as a low concentration catalyst.

With regard to catalyst life, it is necessary for a hydration catalyst to be sufficiently resistant not only to heat but also to hydrolysis with pressurized water and to reductive decomposition with olefins and alcohols at elevated temperatures. Since aliphatic sulfonic acids are generally more thermally stable than the aromatic acids, ion exchange resins consisting of aliphatic sulfonic acids which have improved resistance to heat have been proposed in the art such as British patent specification No. 1,208,144. However, even catalysts of these resins or of ordinary aliphatic sulfonic acids decompose at temperatures higher than 200° C. in the presence of water and, accordingly, the lifetimes of these catalysts are unsatisfactorily short for industrial employment in the preparation of ethanol and isopropanol by a liquid phase hydration with a low concentration of catalyst. On the contrary, the sulfonic acid catalysts of the present invention were surprisingly found to be thermally and chemically stable at temperatures higher than 200° C. in the presence of water, olefin and alcohol, and substantially no decomposition was detected in life tests extending over long periods of time.

The present invention is predicated on the discovery that the acidity and stability of the sulfonic acid radicals are increased by introducing electron attractive groups in a neighboring position of the sulfonic acid radicals, and it has also been noted that sulfonic acids combined with trifluoromethyl groups or difluoromethylene groups which are among the most strongly electronattractive groups known, provide extremely strong acidity and exhibit excellent heat stability as compared with the original nonfluorine-substituted sulfonic acids, thus obtaining the hydration catalysts of the present invention. In this connection, trifluoromethane sulfonic acid, for example, which is the simplest example of the catalysts of the present invention, exhibits about 25 times the acidity of non-fluorine-substituted methanesulfonic acid, 14 times the acidity of sulfuric acid and 48 times the acidity of hydrochloric acid. Although the high hydration catalytic activity thereof will become apparent from the following examples, it is noted that in a hydration reaction of propylene, conversion of the propylene of as high as 66% (selectivity of 97% to isopropanol) was found to be attained at a reaction temperature of 200° C. when using the catalyst only in an amount of 0.30% by weight of the water used as starting material.

The hydration reaction of olefins using a known solid acid catalyst in the liquid phase or mixed phase has previously been carried out under relatively high temperature and pressure conditions. However, with the hydration reaction of the present invention, the reaction can be conducted at a relatively low temperature under relatively low pressure so that although strongly acidic catalysts are used, only a small amount of ether is produced when suitable reaction conditions are adopted. Thus, substantially no unfavorable low-molecular-weight polymer of the olefin or aldehyde are secondarily produced with an alcohol selectivity higher than 95%.

The hydration reaction is generally carried out at a temperature higher than 200° C. and under acidic conditions as strong as pH 1–4. When known catalysts are employed under such conditions, the material of the apparatus is considerably corroded so that the use of conventional catalysts in industrially disadvantageous. On the other hand, it was found that, in a hydration reaction using the sulfonic acid catalysts of the present invention, when ordinary stainless steel was employed as the apparatus material with reaction temperatures up to about 200° C. or a metal such as titanium with reaction temperatures higher than 200° C., no corrosion occurred.

The present invention will particularly be illustrated by the following examples which are illustrative.

EXAMPLE 1

230 Grams of water, 35.5 grams of liquid propylene (mole ratio of water to propylene being 15.2:1) and 0.6 gram of trifluoromethane sulfonic acid as catalyst (0.26 wt. % based on the water) were introduced into a 370 ml. stainless steel autoclave. The mixture was heated and maintained at a temperature of 200° C. and was agitated for 1.5 hours under a maximum pressure of 160 kg/cm$^2$(G). After recovery or unreacted propylene, 253.6 grams of the reaction solution was obtained. The solution was distilled to give a distillate which was subjected to a gas chromatographic analysis. It was found that 32.9 grams of isopropanol, 0.05 gram of acetone and 0.50 gram of isopropyl ether were obtained without formation of byproducts such as propylene oligomer and the like. The conversion of the propylene was 66.5% and selectively to the isopropanol was 97.7%. The residue obtained after distillating the products of isopropanol, etc., from the reaction solution showed a pH value of 1.6 which was not changed before or after the reaction. By analysis, it was found that the catalyst used was not decomposed.

When the residue was reused as a catalyst aqueous solution and the reactions were repeated in the same manner as above, the results remained substantially the same. Moreover, when the material corrosion test was made under the reaction conditions of this example, no corrosion on the stainless steel of the autoclave was observed.

EXAMPLE 2

Example 1 was repeated except that perfluoroethane sulfonic acid was used as catalyst with the result that the conversion of propylene was 65.5% and the selectivity to isopropanol was 97.1%.

EXAMPLE 3

Example 1 was repeated except that perfluorooctane sulfonic acid was used as catalyst and the reaction was conducted at 205° C. for 1 hour, with the result that the conversion of propylene was 60.0% and the selectivity to isopropanol was 97.0%.

EXAMPLE 4

Example 1 was repeated except that difluoromethane sulfonic acid was used as catalyst, with the result that the conversion of propylene was 53.5% and the selectivity to isopropanol was 98.0%.

EXAMPLE 5

Example 1 was repeated except that chlorofluoromethane sulfonic acid was used as catalyst, with the result that the conversion of propylene was 55.8% and the selectivity to isopropanol was 98.4%.

EXAMPLE 6

Example 1 was repeated except that cyclohexyldifluoromethane sulfonic acid was used as catalyst and the reaction was conducted at 210° C. for 1 hour, with the result that the conversion of propylene was 51.5% and the selectivity to isopropanol was 97.1%.

EXAMPLE 7

Example 1 was repeated except that perfluorophenylmethane sulfonic acid was used as catalyst, with the result that the conversion of propylene was 50.4% and the selectivity to isopropanol was 97.3%.

EXAMPLE 8

0.15 Gram of trifluoromethane sulfonic acid (0.30 wt. % based on the water), 50 grams of water and 11.0 grams of ethylene (mole ratio of 7.1:1) were introduced into a 100 ml. stainless steel autoclave and the mixture was agitated at a temperature of 280° C. for 4 hours under a maximum pressure of 340 kg/cm$^2$(G). It was found by gas chromatographic analysis that 8.08% by weight of ethanol was contained in 53 grams of the reaction solution. The conversion of ethylene was 25.1% and the selectivity to ethanol was 94.5%.

EXAMPLE 9

1,400 Grams of an aqueous solution containing 0.5% by weight of trifluoromethane sulfonic acid were placed in a 3 liter titanium-lined antoclave and was heated to 290° C. Ethylene was charged until the pressure in the autoclave reached 300 kg/cm$^2$(G). When the mixture was agitated for 100 minutes at that temperature, the pressure dropped to 155 kg/cm$^2$(G). Then the solution was rapidly cooled and the residual gas was released. The analyses revealed that 1,536 grams of the reaction solution contained therein 14.4% by weight of ethanol and 3.6% by weight of ether. Byproducts such as an ethylene oligomer, aldehydes or the like were not observed and the conversion of ethylene was 65.0%.

EXAMPLE 10

An aqueous solution containing 0.3% by weight of trifluoromethane sulfonic acid and ethylene were continuously fed into a 100 ml. titanium alloy reactor at rates of 89.1 g/hr and 16.9 g/hr, respectively, (mole ratio of 8.0:1) and the mixture was reacted at 300° C. under a pressure of 260 kg/cm$^2$(G). The reaction product was then transferred to a vapor-liquid separator and the vapor and the liquid were separated from each other at room temperature under pressurized conditions. Unreacted gases were released through a regulating valve and the liquid was collected in the form of an alcohol solution. The reaction product contained therein 8.80% by weight of the corresponding alcohol and 950 ppm. of the ether. This result gave an ethylene conversion of 30% and an ethanol selectivity of 98.9%.

EXAMPLE 11

0.20 Gram of difluoromethionic acid (0.4 wt. % based on the water) as catalyst, 50 grams of water and 11.5 grams of ethylene (mole ratio of 6.8:1) were introduced into a 100 ml. titanium alloy autoclave and the mixture was agitated at 270° C. for 3 hours under a maximum pressure of 310 kg/cm$^2$(G). The resultant reaction solution contained therein 6.5% by weight of ethanol with an ethylene conversion of 18% and ethanol selectivity of nearly 100%.

EXAMPLE 12

0.55 Gram of trifluoromethane sulfonic acid (1.0 wt. % based on the water), 55 grams of water and 24.5 grams of isobutylene (mole ratio of 7.0:1) were used and the reaction was carried out in the same manner as in Example 8 at a temperature of 150° C. for 3 hours under a maximum pressure of 154 kg/cm$^2$(G). The yield of tertiary butanol was 11.6% and the selectivity to tertiary butanol was nearly 100%.

EXAMPLE 13

Example 12 was repeated except that 1-butene was used instead of isobutylene and the reaction was conducted at 200° C. under a maximum pressure of 220 kg/cm$^2$(G), with the result that the yield of the secondary alcohol was 12.6% and selectivity to the secondary butanol was nearly 100%.

EXAMPLE 14

Example 8 was repeated except that 20 grams of 1-octene was used (mole ratio of 15.6:1) and the reaction was conducted at 250° C. for 3 hours under a maximum pressure of 54 kg/cm$^2$(G) to give 69.5 grams of reaction product. Gas chromatographic analyses revealed that the reaction product contained therein 2.3% by weight of 2-octanol. Conversion of 1-octene was 6.9% and the selectivity to octanol was nearly 100%.

EXAMPLE 15

4.0 Grams of an aqueous solution containing 1% by weight of trifluoromethane sulfonic acid and 5.0 grams of 1-tetradodecene (mole ratio of 8.7:1) were introduced into a 100 ml. titanium alloy autoclave and the mixture was agitated at 250° C. for 3 hours under a maximum pressure of 35 kg/cm$^2$(G) to give a 4.6 grams organic layer of reaction product. Gas chromatographic analyses revealed that the organic layer contained therein 1.0% by weight of tetradecanol.

EXAMPLE 16

Example 15 was repeated except that 1-octadecene in a mole ratio to water of 11.2:1 was used in lieu of 1-tetradecene under pressure of 35 kg/cm$^2$(G) to give a 4.7 gram organic layer of reaction product. The organic layer contained therein 1.2% by weight of octadecanol.

EXAMPLE 17

0.55 gram of perfluorobutane-1,4-disulfonic acid (1.0 wt. % based on the water) as catalyst, 55 grams of water and 20.0 grams of liquified propylene (mole ratio of 6.4:1) were introduced into a 100 ml. titanium alloy autoclave, and the mixture was agitated at 230° C. for 2 hours under a maximum pressure of 270 kg/cm$^2$(G). Analyses of the unreacted gas and the liquid product by gas chromatography revealed that the conversion of propylene was 71.0% and the selectivities to isopropanol and isopropyl ether were 75.1% and 20.5%, respectively.

EXAMPLE 18

Example 17 was repeated except that 1,4-bis(sulfodifluoromethyl)benzene was used as catalyst, with the result that the conversion of propylene was 69.5% and the selectivities to isopropanol and to isopropyl ether were 80.9% and 14.2%, respectively.

EXAMPLE 19

Example 17 was repeated except that 0.55 gram of trifluoromethane sulfonic acid was used as catalyst and the reaction was conducted at 250° C. for 2 hours under a pressure of 280 kg/cm$^2$(G) with the result that the conversion of propylene was 75.0% and the selectivities to isopropanol and to isopropyl ether were 65.0% and 31.8%, respectively.

EXAMPLE 20

0.50 Gram of trifluoromethane sulfonic acid (1.0 wt. % based on the water) as catalyst, 50 grams of water and 10.0 grams of ethylene (mole ratio of 7.8:1) were introduced into a 100 ml. titanium alloy autoclave, and the mixture was agitated at 300° C. for 2 hours under a maximum pressure of 300 kg/cm$^2$(G). By analyzing the unreacted gas and the reaction product by gas chromatography, it was found that the conversion of ethylene was 69.1% and the selectivities to ethanol and to the ether were 66.2% and 31.5%, respectively.

EXAMPLE 21

The following experiment was carried out in order to determine stability of the catalysts of the present invention. 62 Grams of a 0.30 wt. % aqueous solution of trifluoromethane sulfonic acid was reacted with 10 grams of propylene (mole ratio of 14.5:1) at 200° C. under a maximum pressure of 165 kg/cm$^2$(G) for 1 hour in the same manner as in Example 17. As a result, it was found that the propylene conversion rate was 62%, and the isopropanol selectivity was 98.5%. By titrating the acid value of the catalyst in the reaction solution, 99.5% of the acid was found remaining. In view of possible experimental error, decomposition of the catalyst was considered to take place only to the extent that it was substantially negligible.

COMPARATIVE EXAMPLE

A comparative experiment was carried out using p-toluene sulfonic acid as typical of heretofore known sulfonic acid catalysts. The reaction was effected in substantially the same manner as in Example 21 except that a 0.31 wt. % aqueous solution of p-toluene sulfonic acid was used. As a result, it was found that the propylene conversion rate was 35% and the isopropanol selectivity was 96%. Only 76.0% of the acid was found remaining in the reaction solution.

EXAMPLE 22

The following experiment was carried out in order to determine stability of the catalyst during the hydration of ethylene at a high temperature.

In the same manner as in Example 17, 40 grams of a 0.30 wt. % aqueous solution of trifluoromethane sulfonic acid was reacted with 10 grams of ethylene (molar ratio of 6.2:1) at a temperature of 300° C. under a maximum pressure of 270 kg/cm$^2$(G) for 8 hours. It was found that the ethylene conversion rate was 50%, the ethanol selectivity was 81.3% and the ethyl ether selectivity was 17.0%. After the reaction, 101% of the acid was titrated in the reaction solution. In view of possible experimental errors, decomposition of the catalyst was considered to take place only to the extent that it was substantially negligible.

What is claimed is:

1. In the direct hydration of an olefin having from 2 to 20 carbon atoms with water under liquid phase hydration conditions to form an alcohol, the improvement comprising, the step of conducting said direct hydration at a temperature of 100° to 350° C., a pressure of 1 to 500 kg/cm$^2$(G) and a mole ratio of water to olefin of 1:1 to 20:1 while the olefin is in contact with a catalytic amount in the range of 0.01 to 2% by weight of said water in the reaction system of a sulfonic acid catalyst represented by the general formulae (1) or (2)

$$ACF_2SO_3H \qquad (1)$$

$$B(CF_2SO_3H)_n \qquad (2)$$

wherein A represents hydrogen, halogen, a sulfonic radical, a sulfodifluoromethyl radical or a monovalent unsubstituted aliphatic, alicyclic or aromatic residue consisting of hydrocarbon or fluorohydrocarbon radicals containing less than 20 carbon atoms and B represents a di-, tri- or tetravalent unsubstituted aliphatic, alicyclic or aromatic residue consisting of hydrocarbon or fluorohydrocarbon radicals containing less than 20 carbon atoms in direct correspondence to the value of $n$ being 2,3 or 4, said sulfonic acid catalyst being thermally and chemically stable at temperatures higher than 200° C in the presence of said water, said olefin and said alcohol.

2. The method according to claim 1 wherein said catalyst is trifluoromethane sulfonic acid.

3. The method according to claim 1 wherein said catalyst is perfluoroethane sulfonic acid, perfluoropropane sulfonic acid or perfluorobutane sulfonic acid.

4. The method according to claim 1 wherein said catalyst is perfluoroethane-1,2-disulfonic acid.

5. The method according to claim 1 wherein said catalyst is difluoromethionic acid.

6. The method according to claim 1 for the production of ethyl alcohol from ethylene wherein the hydration is conducted at a temperature of from 250° to 300° C. under a pressure of 200 to 350 kg/cm$^2$(G) in the presence of trifluoromethane sulfonic acid.

7. The method according to claim 1 for the production of isopropyl alcohol from propylene wherein the hydration is conducted at a temperature of from 150° to 250° C. under a pressure of 150 to 300 kg/cm$^2$(G) in the presence of trifluoromethane sulfonic acid.

* * * * *